United States Patent [19]
Angstadt et al.

[11] Patent Number: 5,491,278
[45] Date of Patent: Feb. 13, 1996

[54] ALKYLATION PROCESS USING SOLID SUPERACID CATALYST LIQUID PHASE

[75] Inventors: Howard P. Angstadt, Media, Pa.; Elmer J. Hollstein, Wilmington, Del.; Chao-Yang Hsu, Media, Pa.

[73] Assignee: Sun Company, Inc. (R&M), Philadelphia, Pa.

[21] Appl. No.: 151,718

[22] Filed: Nov. 12, 1993

[51] Int. Cl.$^6$ ................................. C07C 2/62
[52] U.S. Cl. ............................ 585/731; 585/730
[58] Field of Search ...................... 585/730, 731

[56] References Cited

U.S. PATENT DOCUMENTS

| | | |
|---|---|---|
| 4,918,041 | 4/1990 | Hollstein et al. . |
| 4,956,519 | 9/1990 | Hollstein et al. . |
| 5,036,035 | 7/1991 | Baba et al. . |
| 5,212,136 | 5/1993 | Angstadt et al. . |
| 5,214,017 | 5/1993 | Angstadt et al. . |
| 5,321,196 | 6/1994 | Ohgoshi et al. ............ 585/709 |
| 5,321,197 | 6/1994 | Angstadt et al. ............ 585/721 |
| 5,324,881 | 6/1994 | Kresge et al. ............... 585/721 |
| 5,391,532 | 2/1995 | Soled et al. . |
| 5,420,092 | 5/1995 | Soled et al. . |
| 5,422,327 | 6/1995 | Soled et al. . |

FOREIGN PATENT DOCUMENTS

| | | |
|---|---|---|
| 61-183230 | 8/1986 | Japan . |
| 61-242641 | 10/1986 | Japan . |
| 1-245853 | 10/1989 | Japan . |
| 1-245854 | 10/1989 | Japan . |

OTHER PUBLICATIONS

Ito et al., "Solid acid catalysts for isobutane alkylation", *CA Selects, Abstract No. 106*:216817b, Issue 13, 20, (1987).
"Superacids Catalyze Alkylation of Xylene", *Chemical Week*, Nov. 25, 1987, p. 28.

Primary Examiner—Asok Pal
Attorney, Agent, or Firm—Q. Todd Dickinson; Stephen T. Falk

[57] ABSTRACT

Isoparaffins and olefins are alkylated in the liquid phase by contact with a solid superacid such as sulfated zirconia containing heteropolyacids or polyoxoanions. High octane number blending components for motor fuel and other valuable products are obtained, with important advantages over processes using liquid acid catalysts, and over vapor phase alkylation with solid superacid catalysts.

12 Claims, 1 Drawing Sheet

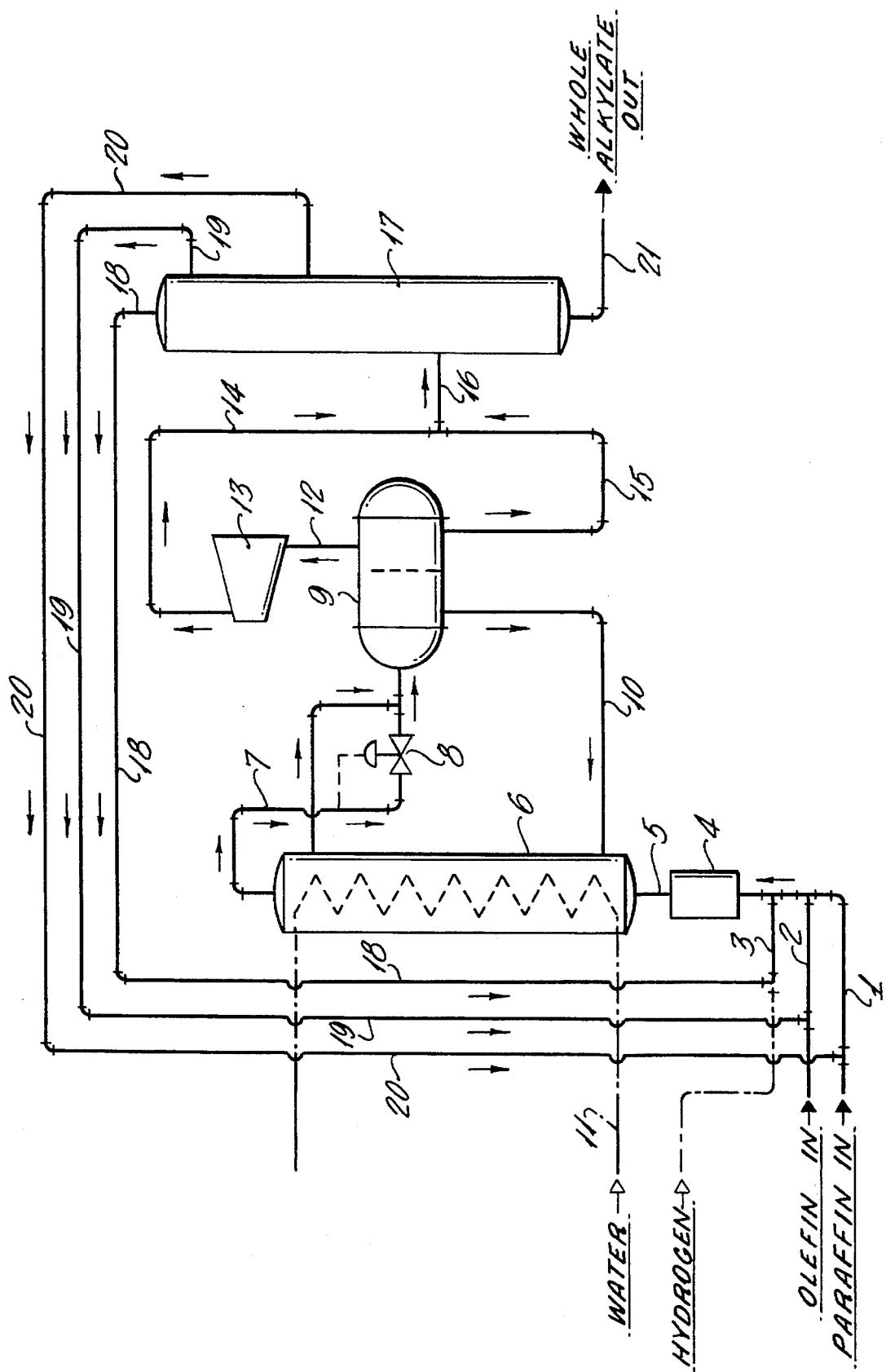

5,491,278

ALKYLATION PROCESS USING SOLID SUPERACID CATALYST LIQUID PHASE

BACKGROUND OF THE INVENTION

Alkylation as referred to herein is the reaction of paraffins with olefins to produce a mixture of highly branched paraffins called alkylate. The major use of the alkylation process is to produce alkylate for gasoline blends. At present, the only alkylation processes of commercial interest use sulfuric acid or hydrofluoric acid as catalysts. These catalysts are currently used because they are more competitive with respect to economics and alkylate quality than any other catalyst system developed to this date.

Use of sulfuric acid and hydrofluoric acid as catalysts for alkylation, however, is fraught with safety and environmental problems. The feedstocks, products, and catalysts are liquids and require substantial processing equipment to separate them. Further, the catalysts are corrosive and toxic and must be handled with great care to contain and to regenerate or dispose of them.

THE PRIOR ART

Solid superacid catalysts have been proposed for use as alkylation catalysts. See for example Hollstein et al U.S. Pat. Nos. 4,918,041 and 4,956,519 issued Apr. 17, 1990 and Sep. 11, 1990 respectively, disclosing solid superacid catalysts useful in alkylation and other reactions comprising a sulfated calcined metal oxide or hydroxide of Group III or Group IV, e.g. zirconium; metal oxide or hydroxide of Group V, Group VI or Group VII; e.g. manganese, metal oxide or hydroxide of Group VIII, e.g. iron. See also Angstadt et al U.S. Pat. No. 5,212,136 issued May 18, 1993, disclosing solid superacid catalysts useful as alkylation catalysts comprising sulfated and calcined mixtures of a support comprising an oxide or hydroxide of a Group IV-A element, an oxide or hydroxide of molybdenum and an oxide or hydroxide of a Group I-B, II-B, III-A, III-B, IV-B, V-A or VI-A metal other than molybdenum, or a metal of the Lanthanide Series of the Periodic Table. See also Angstadt et al U.S. Pat. No. 5,214,017 issued May 25, 1993, disclosing solid superacid catalysts useful as alkylation catalysts, comprising sulfated and calcined mixtures of a support comprising an oxide or hydroxide of a Group IV-A element, an oxide or hydroxide of Group VI, VII or VIII metal, an oxide or hydroxide of a Group I-B, II-B, III-A, III-B, IV-B, V-A or VI-A metal and an oxide or hydroxide of a metal of the Lanthanide Series of the Periodic Table.

Other disclosures of solid superacids useful in alkylation processes are contained in:

(1) Hatakeyama et al Japanese Kokai Patent, SHO 61-183230, Aug. 15, 1986, disclosing sulfated zirconia alkylation catalysts and their use in alkylation of butenes and isobutane at a temperature in the range from −20° C. to +10° C. under pressure of from 0 to 50 kg kg/cm², the alkylation being carried out in either gaseous phase or liquid phase, the latter preventing inactivation that is caused by deposition of coke on the catalyst and extending the life of the catalyst, and the reaction being carried out either by a suspension or fixed bed process.

(2) Abstract No. 106:216817b, CA Selects: Catalysis (Applied Physical Aspects), Issue 13, Jun. 29, 1987, Ito et al, Jpn. Kokai Tokyo Koho JP 61,242,641 (86,242,641), Oct. 28, 1986, disclosing alkylation catalysts prepared from sulfate ion or its precursors and rare earth metals or their compounds, e.g. lanthanum nitrate, on supports consisting of Group IV-A or IV-B metal hydroxides or oxides, followed by calcination and stabilization, and the use of such catalysts in alkylation of isobutane with isobutene at 60° C.

(3) In the corresponding Ito et al Japanese Kokai Patent, SHO 61-242641, Oct. 28, 1986, application SHO 60-84515 filed Apr. 22, 1985, a solid acidic catalyst for alkylation of isoparaffin with olefin is disclosed. The catalyst is obtained by adding a rare earth element or its compounds, and sulfate radical or its precursor to a supporting member made of hydroxide or oxide of Group IV metals, followed by sintering at 400°–800° C. for stabilization. Hydroxide or oxide of at least one type of metal chosen from titanium, zirconium, hafnium, silicon, germanium and tin is used; particularly hydroxide or oxide of zirconium or titanium is preferred. Tantalum and cerium or their compounds are disclosed, as the most desirable rare earths; praseodymium, neodymium, samarium and gadolinium are also disclosed. The alkylation reaction is preferably run in liquid phase.

(4) In Hosoi et al Japanese Kokai Patent HEI 1-245853 disclosure date Oct. 2, 1989, Application No. SHO 63-73409, Mar. 29, 1988, solid acid catalyst for alkylation is disclosed, containing a Group IIb, Group Va, Group VIa or Group VIIA metal or compound thereof, and sulfate or precursor of sulfate, on a carrier made from hydroxide or oxide of Group III and/or Group IV metals, followed by baking and stabilizing. Sulfated zinc/zirconium hydroxides, chromium/zirconium hydroxides, vanadium/zirconium hydroxides, manganese/zirconium hydroxides, zinc/titanium hydroxides, zirconium/titanium hydroxides, zirconium/aluminum hydroxides are disclosed. It is desirable to run the reaction in liquid phase.

(5) In Shimizu et al Japanese Kokai Patent HEI 1-245854, disclosure date Oct. 2, 1989, Application No. SHO 63-73410, Mar. 29, 1988, a solid acid catalyst for alkylation of isobutane by olefins is obtained by adding a sulfate or precursor thereof to a carrier comprising compound metal hydroxides or compound metal oxides of two or more kinds of metals selected from titanium, zirconium, silicon and tin. Sulfated zirconia/titania, zirconia/tin oxide, zirconium/silicon catalysts are disclosed. Running the reaction in liquid phase is disclosed as desirable.

(6) Chemical Week, Nov. 25, 1987, on page 28, discloses superacids obtained by sulfating zirconium, titanium and iron oxides, as catalysts for alkylation of orthoxylene by styrene.

DESCRIPTION OF THE INVENTION

The present invention provides an alkylation method which minimizes the processing problems of the existing commercial methods using sulfuric acid or HF and which combines the benefits of solid superacid catalysts with the benefits of adding heteropolyacid components (HPA's) or polyoxoanion components (POA's) to the catalyst with the benefits of liquid phase operation.

The method of the invention employs solid superacid catalysts comprising sulfated oxide or hydroxide of a Group III or Group IV element, for example zirconium, though other Group III or IV elements or mixtures of such elements can be employed. The solid superacid catalyst used according to the process of the invention, contains in addition to such sulfated Group III or IV element, an HPA or POA as subsequently described. The method of the invention is carried out in liquid phase, preferably through a fixed-bed reactor, and under super atmospheric pressure. Since the catalyst in this embodiment is a solid, only reactants and products need be separated. The solid catalyst used in the method of the invention is superior to catalysts used previously for alkylation in respect of environmental and safety concerns and, when spent, can be regenerated in the same reactor or reprocessed off-site.

The alkylate produced by the HPA- or POA-modified sulfated zirconia has a higher proportion of 8-carbon compounds than that obtained when using only the sulfated zirconia, and the proportion of the 8-carbon fraction containing the high octane trimethylpentanes is also greater than that obtained either with the more traditional acids or the unmodified solid superacids. Additionally the amount of heavier ends, $C_9$–$C_{12}$, produced during the alkylation is greatly reduced. The alkylation reaction can be carried out at room temperature to provide good yields of alkylated, thus eliminating the need for sub-ambient cooling and resulting in a more energy efficient operation.

PREPARATION OF SUPERACID HPA OR POA CATALYST

The solid superacid catalyst used according to the invention is prepared by incorporating an HPA or POA onto a sulfated zirconia or other Group III or IV oxide support by techniques known to those skilled in the art of catalyst preparation. Techniques for preparing sulfated and calcined solid superacids comprising oxides of Group III or IV elements such as zirconia are disclosed for example in the Hollstein et al and Angstadt et al patents supra, the disclosures of which are hereby incorporated by reference. The incorporation of HPA or POA into the catalyst is typically done by forming an aqueous solution of an ammonium salt of the HPA or POA and impregnating the solid superacid with the solution; typically the impregnation is done by the incipient wetness technique in which the amount of water used to make the solution is about the amount which will be absorbed by the solid superacid upon contact of the latter with the solution. The order of the sulfating and calcining of the catalyst in relation to the impregnation of the Group III or IV oxides with HPA or POA is not critical; however it is preferred to impregnate the Group III or IV oxide with HPA or POA following the sulfation of the Group III or IV oxide and prior to the final calcining of the composition.

The weight of HPA or POA relative to Group III or IV oxide in the composition according to the invention will typically be in the range from about 0.1% to about 10%, preferably 0.5% to 5%, but any suitable ratio may be used. Since the HPA or POA is typically more expensive to manufacture than the Group IV oxide, it is preferred to use the minimum amount of HPA or POA consistent with the desired activity of the composition as a catalyst for improvement of isomer distribution in the alkylation product.

Preferred HPA's or POA's for use according to the invention are those having the Keggin structure represented by the formula $H_4XM_{12}O_{40}$, wherein X may be any metal from Groups IV, V, VI, VIII, or the Lanthanide series of the Periodic Table, and M is any element in Groups III, IV, V, or VI; however, heteropoly acids of the Anderson and Dawson types are also anticipated to produce effective alkylation catalysts when placed upon a solid superacid support. Alkylation results are given in Table I showing that the catalyst compositions of the invention provide higher concentrations of 8-carbon containing species and lower concentrations of $C_9$–$C_{12}$ heavy products than does a catalyst prepared from the super-acid zirconia support alone and than are produced using the traditional sulfuric or HF acid processes. Additionally, the amount of the high octane trimethylpentanes produced within the 8-carbon fraction is also significantly greater than that obtained from the traditional processes, thus leading to a higher octane alkylate. The support upon which the HPA or POA is incorporated need not be entirely composed of one component such as sulfated zirconia. Mixtures of zirconia with other appropriate oxides such as the oxides from elements in Groups III-A and B and IV-A and B of the Periodic Table may be used. Mixtures of these oxides along with zirconia, upon impregnation with the appropriate HPA or POA and sulfating, provide superior solid-acid alkylation catalysts. For example, silica-zirconia, titania-zirconia, alumina-zirconia, hafnia-zirconia represent appropriate supports for sulfation and impregnation with in the scope of the invention. In place of zirconia, other Group III-A and B and Group IV-A and B oxides, or mixtures thereof, may be employed.

The HPA or POA which is used in the catalyst according to the invention may be (1) an azide-promoted HPA or POA as disclosed in Lyons et al U.S. Pat. No. 4,803,187 issued Feb. 7, 1989, the formula of which is disclosed as $K_6PW_{11}VO_{40}N_3$, (2) a site-specific framework-substituted HPA or POA as disclosed in Ellis et al U.S. Pat. No. 4,898,989 issued Feb. 6, 1990, wherein three atoms of molybdenum, tungsten, vanadium or combinations thereof have been replaced with three different metal atoms, which may be for example iron, nickel, zinc, chromium or combinations thereof, (3) HPA's having the formula $H_z(X_kM_nO_y)$ where X is a group IIIA–VIA element, M is a transition metal, k is 1–5, n is 5–20, y is 18–62, and z is 1–6, and corresponding POA's as disclosed in Lyons et al U.S. Pat. No. 4,916,101 issued Apr. 10, 1990, (4) site-specific, framework substituted HPA's or POA's wherein three atoms of molybdenum, tungsten or vanadium or combinations thereof have been replaced with three different metal atoms, two of which are selected from the group consisting of iron, chromium, manganese and ruthenium, and the third of which is different from said two and is selected from the group consisting of transition metals, and in addition to (1) to (4), the prior art HPA and POA referred to in (1) to (4), such as Heteropoly and Isopoly Oxo-metalates, Pope et al, Springer-Verlag, New York, 1983. HPA's and POA's generally are suitable for use in the catalysts according to the invention, while the HPA's and POA's disclosed in (1) to (4) above are preferred.

ALKYLATION METHOD OF TEE INVENTION

In the method according to the invention, a feedstock comprising isoparaffins and olefins is contacted with a solid superacid catalyst containing sulfated Group III or IV element and HPA or POA under conditions to maintain the feedstock in liquid phase, those conditions including temperatures and pressures as disclosed below. The liquid phase operation according to the invention provides advantages over the prior art vapor phase operation in that equipment costs and utility costs are lower, and lower catalyst deactivation rates result.

The invention provides in one embodiment an improved method for the production of alkylate which comprises alkylating a paraffin with an olefin at alkylation conditions which include a paraffin to olefin volume ratio of about 1:1 to about 100:1, a temperature of from about –40° C. to about 200° C., a pressure of from about 1 atmosphere to about 200 atmospheres, a liquid hourly space velocity of from about 0.01 to about 30 in the presence of a solid superacid catalyst containing HPA or POA as herein specified, which may or may not be attended by the presence of hydrogen in the feed. Preferred temperatures and pressures are from about −25° C. to about 125° C. and from about 5 to about 50 atmospheres. The alkylation can be carried out either in the presence or in the absence of an added gas such as hydrogen. Reactor effluents pass to a distillation column wherein unreacted reactants are separated from products and recycled through the reactor and products are passed to gasoline-making facilities.

BRIEF DESCRIPTION OF THE DRAWING

The invention will be further described with reference to the attached drawing, FIG. 1, which is a schematic diagram of a process conducted according to the invention.

Paraffins are supplied to mixer 4 via line 1. The preferred paraffins include ethane, propane, n-butane, isobutane, pentanes, hexanes and mixtures thereof. Olefin is supplied to mixer via line 2. The preferred olefins are olefinic hydrocarbons which contain one double bond per molecule and include ethylene, propylene, 1-butene, 2-butene, isobutene, pentenes, hexenes and mixtures thereof. The purpose of mixer 4 is to mix thoroughly the paraffin and olefin feeds and, if used, hydrogen prior to contacting with the catalyst. Mixer 4 may be of the in-line or mechanically-driven type.

The alkylation reaction takes place in reactor 6. Reactants are supplied to reactor 6 via line 5 after being mixed in mixer 4. The alkylation reaction is highly exothermic with, for example, the liberation of 124,000 to 140,000 BTU per barrel of isobutane reacting. Reaction temperature is controlled in the reactor by use of cooling bundles. Water may be supplied as coolant to the cooling bundles but coolant may alternatively be provided by reactor effluent as is shown in FIG. 1. The reactor effluent flows through a pressure-reducing valve 8 via line 7 to a flash drum/suction trap 9. A portion of the effluent is flashed and the remaining effluent stream is cooled. The cold effluent liquid flows through line 10 to the cooling bundles. The flashed gases are compressed in compressor 13, liquefied, combined with the remaining reactor effluent and sent via line 16 to the deisobutanizer column 17 where alkylate is removed as product and unreacted reactants are recycled to the reactor through lines 18, 19, and 20. Whole alkylate is removed through line 21.

Olefin feed may be pulsed into the reactor by alternately stopping and starting the olefin pump at various time intervals. While this may change the paraffin olefin ratio it serves to flush the surface of the catalyst with paraffin-rich liquid which removes potential coke-forming moieties.

The catalyst may be regenerated in the reactor by heating it to about 400° C. in the presence of dilute air. Alternatively, the catalyst may be removed and regenerated off-site.

EXAMPLES

The following examples illustrate the invention.

Example I

A mixed feed of isobutane and propylene at a volume ratio of 20:1 was charged upflow through a fixed-bed reactor containing 10.0 ml of catalyst at 20° C. and 300 psig. At these conditions, reactants and products are in liquid phase. The reaction was monitored by taking liquid samples hourly and subjecting them to gas chromatographic analysis. The results are shown in Table I.

TABLE I

OCTANE CALCULATION: C3/C4-FREE ALKYLATION
REACTION NUMBER: 977118
CATALYST NO.: 975568
CATALYST DESCRIPTION: 2% Mo(HPA)/4% SO4/ZrO2/726
FEEDSTOCKS: 10:1 iC4:C3 =

| COMPOUND | B-OCT | M-OCT | R-OCT | 60.00 | 120 | 180 | 240 | 300 | 360 | 420 |
|---|---|---|---|---|---|---|---|---|---|---|
| nC4 | 113 | 89.6 | 94.0 | 0.00 | 0.00 | 0.00 | 0.00 | 0.00 | 0.00 | 0.00 |
| 1C4 | 122 | 97.6 | 102.1 | | | | | | | |
| TOT C4 | | | | | | | | | | |
| 2MC4 | 100 | 89.7 | 98.0 | 20.60 | 44.02 | 41.53 | 32.93 | 10.01 | 5.21 | 1.76 |
| OTHER C5 | 100 | 80.2 | 85.5 | | | 0.13 | 0.18 | 0.52 | 1.33 | |
| TOT C5 | | | | 20.60 | 44.02 | 41.66 | 33.11 | 18.53 | 6.55 | 1.76 |
| 22DMC4 | 84 | 93.4 | 91.8 | 1.78 | 6.52 | 3.88 | 3.08 | 1.39 | | |
| 23DMC4 | 96 | 94.3 | 104.3 | 3.59 | 8.61 | 3.05 | 3.61 | 7.09 | 12.35 | 12.99 |
| 2MC5 | 82 | 73.5 | 73.4 | 2.84 | | 5.12 | 5.04 | | | |
| 3MC5 | 86 | 74.3 | 74.5 | 1.12 | 2.26 | 2.07 | 1.75 | 1.24 | | |
| TOT C6 | | | | 9.33 | 17.39 | 14.11 | 13.48 | 10.52 | 12.35 | 12.99 |
| 22DMC5 | 89 | 95.6 | 92.8 | | 5.72 | 1.36 | 1.60 | | | |
| 24DMC51 | 76 | 83.8 | 83.1 | 5.36 | 3.30 | 3.84 | 3.92 | 3.77 | 1.55 | |
| 223TMC4 | 112 | 101.3 | 112.1 | | | 0.18 | | | | |
| 33DMC5 | 84 | 86.6 | 80.8 | 1.04 | 2.11 | 0.96 | 0.72 | | | |
| 3MC6 | 56 | 55.8 | 52.0 | 0.56 | 1.68 | 0.99 | 0.87 | 0.63 | | |
| 23DMC5 | 88 | 88.5 | 91.1 | 2.35 | 1.62 | 3.59 | 5.34 | 6.20 | 2.55 | |
| 3EC5 | 64 | 69.3 | 65.0 | | 1.36 | 0.82 | 0.72 | .59 | | |
| OTHER C7 | 40 | 46.4 | 42.4 | | | | | | | |
| TOT C7 | | | | 9.31 | 15.79 | 11.73 | 13.17 | 11.19 | 4.11 | |
| 224TMC5 | 100 | 100.0 | 100.0 | 23.01 | 1.88 | 6.08 | 7.39 | 8.77 | 3.43 | |
| 22DMC6 | 87 | 77.4 | 72.5 | 4.06 | 2.27 | 1.10 | 1.06 | 0.99 | | |
| 25DMC6 | 55 | 55.7 | 55.2 | 2.73 | 1.27 | 0.73 | 0.78 | 0.75 | | |
| 24DMC6 | 64 | 69.9 | 65.2 | 4.91 | 0.34 | 0.99 | 1.05 | 1.09 | | |
| 223TMC5 | 104 | 99.9 | 109.6 | 1.18 | 1.37 | 0.29 | | | | |
| 33DMC6 | 72 | 83.4 | 75.5 | 2.27 | | | | | | |
| 234TMC5 | 97 | 95.9 | 102.7 | 5.96 | | 1.48 | 1.83 | 2.18 | | |
| 233TMC5 | 100 | 99.9 | 106.1 | 1.37 | 0.78 | 0.47 | 0.56 | | | |
| 23DMC6 | 70 | 78.9 | 71.3 | | 0.97 | 0.39 | 0.34 | | | |

TABLE I-continued

OCTANE CALCULATION: C3/C4-FREE ALKYLATION
REACTION NUMBER: 977118
CATALYST NO.: 975568
CATALYST DESCRIPTION: 2% Mo(HPA)/4% SO4/ZrO2/726
FEEDSTOCKS: 10:1 iC4:C3=

| COMPOUND | B-OCT | M-OCT | R-OCT | 60.00 | 120 | 180 | 240 | 300 | 360 | 420 |
|---|---|---|---|---|---|---|---|---|---|---|
| 3E2MC5 | 76 | 88.1 | 87.3 | | | 0.11 | | | | |
| 3MC7 | 30 | 35.0 | 26.8 | | | 0.03 | | | | |
| 34DMC6 | 67 | 81.7 | 76.3 | | | | | | | |
| 4MC7 | 30 | 39.0 | 26.7 | | | | | | | |
| 3E3MC5 | 76 | 88.7 | 80.8 | | | | | | | |
| OTHER C8 | 30 | 38.0 | 45.0 | | 0.42 | 0.16 | 0.17 | | | |
| TOT C8 | | | | 45.49 | 9.31 | 11.83 | 13.18 | 13.77 | 3.43 | |
| 225TMC8 | 91 | 91.0 | 96.0 | 1.24 | | 2.20 | 2.41 | 2.18 | | |
| OTHER C9 | 90 | 97.5 | 84.0 | | | 2.97 | 4.58 | 8.39 | 13.87 | 25.04 |
| TOT C9 | | | | 1.24 | 5.17 | 6.99 | 10.57 | 13.87 | 25.04 | |
| TOT C10 | 60 | 80.0 | 86.0 | | | 1.62 | 1.98 | 6.11 | 10.72 | 15.25 |
| TOT C12 | 50 | 60.0 | 60.0 | | | 0.34 | 2.83 | 6.63 | 16.64 | 16.30 |
| CALC RES OCT | | | | 85.97 | 86.51 | 86.46 | 84.74 | 77.32 | 67.66 | 71.34 |

In Table I, the octane number calculations are on the $C_3/C_4$-free product. The catalyst used was 2%Mo(HPA)/4% $SO_4/ZRO_2/725$, where HPA is a heteropolyacid having the formula $H_4SiMO_{12}O_{40}$ and where "725" refers to the temperature of calcination of the catalyst in °C. The catalyst was prepared by mixing aqueous zirconyl nitrate and aqueous ammonium hydroxide to obtain a reaction slurry, which is filtered at pH 7, and the damp filter cake is washed with de-ionized water, pelletized, dried at 150° C., and calcined in an oven at about 500° C. for 4.0 hours. The calcined pellets are added slowly to a beaker containing 1.0 normal sulfuric acid solution. The sulfuric acid is decanted after 2 hours. The pellets are impregnated with an aqueous solution of the ammonium salt of the heteropolyacid $H_4SiMO_{12}O_{40}$. The pellets are dried and calcined at 500° C. for 4 hours. The feed to the alkylation reaction using this catalyst contained a 10:1 ratio of isobutane to propylene.

In Table I, nC4 refers to normal butane, iC4 to isobutane, TOT C4 to total butane, 2MC4 to 2-methylbutane, OTHER C5 to other° pentanes, TOT C5 to total pentanes, 22DMC4 to 2,2-dimethylbutane, 23DMC4 to 2,3-dimethyl butane, 2MC5 to 2-methylpentane, 3MC5 to 3-methylpentane, TOT C6 to total hexanes, 3EC5 to 3-ethylpentane, 223TMC4 to 2,2,3-trimethylbutane and so forth. B-OCT refers to blending octane number, M-OCT to motor octane number, R-OCT to Research octane number. The columns headed B-OCT, M-OCT and R-OCT give the octane numbers for the components listed in the "COMPOUND" column. The columns headed 60.00, 120, 180, 240, 300, 360, 420 show the results after reaction for 60 minutes, 120 minutes and so forth up to 420. The "CALC RES OCT" row gives the calculated Research octane number for the products obtained in each of the columns headed 60 to 420.

Examples 2–5

Similar runs to the run of Example 1 were made with the catalysts as subsequently described, and the results are given in Table II under the headings for Runs Numbers 114, 178, 171 and 179. For comparison, the results of a run using sulfuric acid as catalyst is shown in the column headed "$H_2SO_4$". In Run 114, the catalyst used was a sulfated zirconia prepared as described above, using aqueous ammonium salt of the HPA $H_4SiW_{12}O_{40}$ to impregnate the zirconia pellets prior to the final calcination; the weight of HPA relative to sulfated zirconia in the product composition was about 2%. The catalysts used in Runs 171 and 179 were obtained by similar procedure, using the heteropolyacids $H_4SiMO_{12}O_{40}$ and $H_3PMO_{12}O_{40}$ respectively.

In Table II, each row gives the percent of the indicated component or components in the product of the alkylation. Generally similar notation to that in Table I is used, "Me" being used in Table II where "M" is used, and "Et" in Table II where "E" is used in Table I.

TABLE II

ALKYLATE ISOMER DISTRIBUTION

| | RUN NUMBER | | | | |
|---|---|---|---|---|---|
| | H2SO4 | 114 ZrO2/SO4 | 178 H4SiW12040 | 171 H4SiMo12040 | 179 H4PMo1204 |
| 2-MeC4 | 5.726 | 34.704 | 7.455 | 6.075 | 10.325 |
| OTHER C5 | 0.010 | 0.222 | 0.000 | 0.000 | 0.000 |
| TOTAL C5 | 5.737 | 34.926 | 7.455 | 6.075 | 10.325 |
| 2,2-DMeC4 | 0.001 | 3.715 | 0.170 | 0.078 | 0.369 |
| 2,3-DMeC4 | 5.455 | 2.384 | 1.847 | 1.837 | 2.047 |
| 2-MeC5 | 0.000 | 3.651 | 0.979 | 0.841 | 1.239 |
| 3-MeC5 | 0.548 | 1.497 | 0.553 | 0.494 | 0.650 |
| TOTAL C6 | 6.004 | 11.248 | 3.549 | 3.250 | 4.306 |
| 2,2-DMeC5 | 0.000 | 1.248 | 0.060 | 0.026 | 0.149 |

TABLE II-continued

ALKYLATE ISOMER DISTRIBUTION

| | RUN NUMBER | | | | |
|---|---|---|---|---|---|
| | H2SO4 | 114 ZrO2/SO4 | 178 H4SiW12O40 | 171 H4SiMo12O40 | 179 H4PMo12O4 |
| 2,4-DMeC5 | 3.162 | 4.020 | 4.689 | 3.917 | 4.745 |
| 2,2,3-TMeC4 | 0.246 | 0.213 | 0.102 | 0.113 | 0.114 |
| 3,3-DMeC5 | 0.000 | 0.915 | 0.153 | 0.078 | 0.272 |
| 3-MeC6 | 0.154 | 0.721 | 0.221 | 0.260 | 0.264 |
| 2,3-DMeC5 | 1.813 | 1.553 | 1.455 | 1.577 | 1.503 |
| 3-EtC5 | 0.148 | 0.508 | 0.187 | 0.217 | 0.220 |
| OTHER C7 | 0.000 | 0.074 | 0.000 | 0.000 | 0.000 |
| TOTAL C7 | 5.523 | 9.251 | 6.868 | 6.187 | 7.267 |
| 2,4-TMeC5 | 27.420 | 17.440 | 38.221 | 37.088 | 37.241 |
| 2,2-DMeC6 | 0.011 | 0.896 | 0.196 | 0.191 | 0.290 |
| 2,5-DMeC6 | 4.405 | 1.488 | 1.158 | 1.742 | 1.186 |
| 2,4-DMeC6 | 2.855 | 1.220 | 0.000 | 2.227 | 0.000 |
| 2,2,3-TMeC5 | 1.139 | 5.767 | 11.226 | 7.392 | 10.483 |
| 3,3-DMeC6 | 0.000 | 0.351 | 0.094 | 0.078 | 0.123 |
| 2,3,4-TMeC5 | 16.073 | 3.771 | 10.289 | 13.120 | 8.946 |
| 2,3,3-TMeC5 | 15.794 | 5.712 | 15.549 | 13.631 | 14.086 |
| 2,3-DMeC6 | 2.943 | 0.582 | 1.013 | 1.646 | 0.914 |
| 3-Et-2-MeC5 | 0.091 | 0.037 | 0.051 | 0.078 | 0.044 |
| 3-MeC7 | 0.057 | 0.148 | 0.034 | 0.078 | 0.044 |
| 3,4-DMeC6 | 0.518 | 0.148 | 0.255 | 0.399 | 0.237 |
| 4-MeC7 | 0.050 | 0.129 | 0.034 | 0.069 | 0.035 |
| 3-Et-3-MeC5 | 0.002 | 0.000 | 0.000 | 0.000 | 0.000 |
| OTHER C8 | 0.020 | 0.037 | 0.000 | 0.026 | 0.000 |
| TOTAL C8 | 71.381 | 37.726 | 78.120 | 77.704 | 73.629 |
| 2,2,5-TMeC6 | 2.574 | 3.604 | 1.413 | 1.603 | 1.837 |
| OTHER C9 | 1.462 | 1.922 | 1.149 | 1.750 | 1.318 |
| TOTAL C9 | 4.036 | 5.527 | 2.562 | 3.354 | 3.155 |
| TOTAL C10 | 1.714 | 0.582 | 0.740 | 1.395 | 0.712 |
| TOTAL C12 | 5.226 | 0.471 | 0.698 | 2.010 | 0.633 |
| TOTAL >C12 | 0.364 | 0.000 | 0.000 | 0.000 | 0.000 |
| SUM (AREA %) | 99.984 | 99.732 | 99.992 | 100.035 | 100.026 |
| CALC RES OCT | 93.50 | 92.33 | 98.70 | 96.55 | 98.12 |

The invention claimed is:

1. Method of alkylating isoparaffins and olefins which comprises contacting a feedstock comprising isoparaffins and olefins with a solid superacid catalyst containing heteropolyacid or polyoxoanion under conditions to maintain said feedstock in liquid phase, said conditions including a temperature in the range from about −40° C. to about 200° C. and a pressure in the range from about 1 atmosphere to about 200 atmospheres.

2. Method according to claim 1 wherein said temperature is in the range from about −25° C. to about 125° C., and said pressure is in the range from about 5 atmospheres to about 50 atmospheres.

3. Method according to claim 1 wherein said catalyst is sulfated zirconia, sulfated titania, sulfated iron oxide or halogenated alumina.

4. Method according to claim 3 wherein said catalyst comprises sulfated zirconia.

5. Method according to claim 4 wherein said catalyst comprises an oxide or hydroxide of a group VIII metal.

6. Method according to claim 5 wherein said metal is iron.

7. Method according to claim 5 wherein said metal is cobalt.

8. Method according to claim 3 wherein said catalyst has been sulfated with ammonium sulfate.

9. Method according to claim 1 wherein said catalyst contains 5 to 15 weight percent of sulfate ion.

10. Method according to claim 1 wherein the contacting is in the absence of added gas.

11. Method of alkylating paraffins and olefins which comprises introducing a feedstock containing paraffins and olefins into a fixed bed reactor containing a catalyst comprising solid superacid catalyst and heteropolyacid or polyoxoanion, under conditions to maintain said feedstock at least partially in liquid phase, contacting said feedstock and catalyst under alkylation conditions, removing a mixture of unreacted feedstock and alkylation products from said reactor, flashing gases from said mixture to obtain gaseous overhead and liquid alkylate residue, compressing and liquefying said gaseous overhead to obtain liquefied gases, mixing said liquefied gases and said liquid alkylate residue to obtain a deisobutanizer feed, distilling isobutane from said deisobutanizer feed to obtain an overhead recycle fraction and a deisobutanized liquid alkylate product, and recycling said recycle fraction to said reactor.

12. Method according to claim 11 wherein the ratio of said olefins to said paraffins in said feedstock is periodically increased and decreased to flush the surface of the catalyst with paraffin-rich liquid.

* * * * *